United States Patent [19]

Wong

[11] Patent Number: 4,755,679
[45] Date of Patent: Jul. 5, 1988

[54] METHOD AND APPARATUS FOR MAXIMIZING COUNTS OF A PET CAMERA

[76] Inventor: Wai-Hoi Wong, 7903 Deer Meadow, Houston, Tex. 77071

[21] Appl. No.: 876,066

[22] Filed: Jun. 19, 1986

[51] Int. Cl.⁴ .............................................. G01T 1/161
[52] U.S. Cl. ................................ 250/363 S; 250/366; 128/654
[58] Field of Search ................. 250/363 SA, 363 SR, 250/367, 366; 128/654, 655

[56] References Cited

U.S. PATENT DOCUMENTS

| | | | |
|---|---|---|---|
| 4,562,829 | 1/1986 | Bergner | 128/1.1 |
| 4,563,582 | 1/1986 | Mullani | 250/363 S |
| 4,585,009 | 4/1986 | Barker et al. | 128/655 |
| 4,585,941 | 4/1986 | Bergner | 250/363 S |
| 4,642,464 | 2/1987 | Mullani | 250/363 SA |

FOREIGN PATENT DOCUMENTS

| | | | |
|---|---|---|---|
| 3378 | 1/1984 | Japan | 250/363 SR |
| 20881 | 2/1984 | Japan | 250/363 SR |

Primary Examiner—Janice A. Howell
Assistant Examiner—Constantine Hannaher
Attorney, Agent, or Firm—Fulbright & Jaworski

[57] ABSTRACT

The method and apparatus of operating a positron emission tomography camera for measuring concentrations of positron emitting radioisotopes which measures radiation from a patient including true counts, scatter counts and random counts through an energy acceptance window in which the camera has a maximum camera transfer capability of measuring counts. The method and apparatus includes measuring the total counts of radiation and varying the energy acceptance window to accept the total counts available at the maximum camera transfer capability thereby minimizing the random and scattered counts and maximizing the true counts. The method further includes injecting an amount of radiation into the patient sufficient to initially saturate the maximum camera transfer capability. The energy acceptance window is varied by the measurement of total counts.

6 Claims, 7 Drawing Sheets

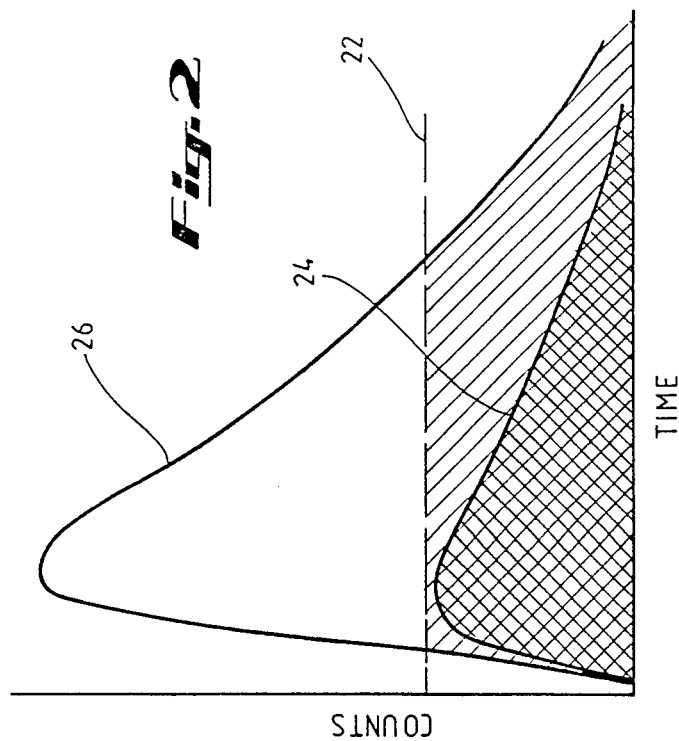
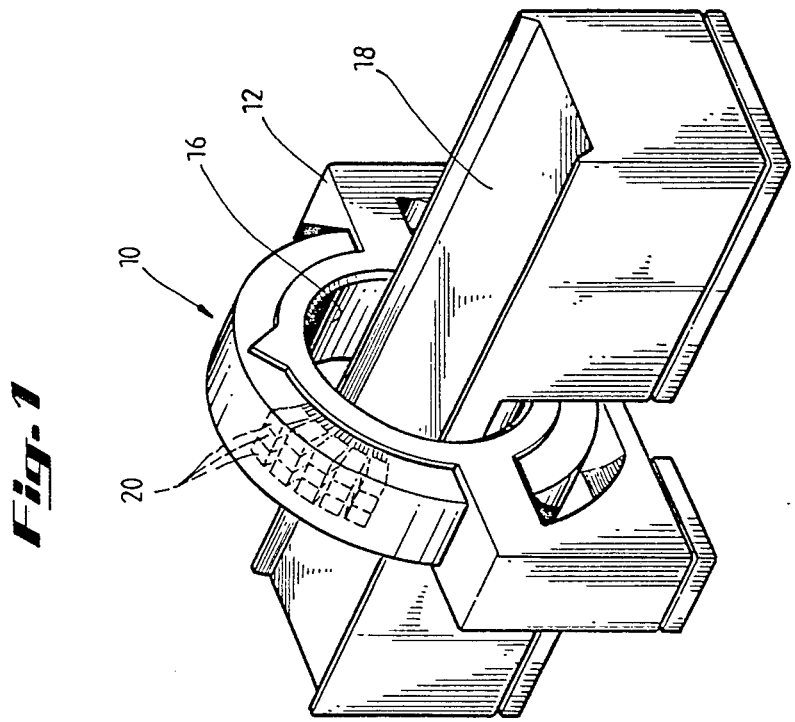

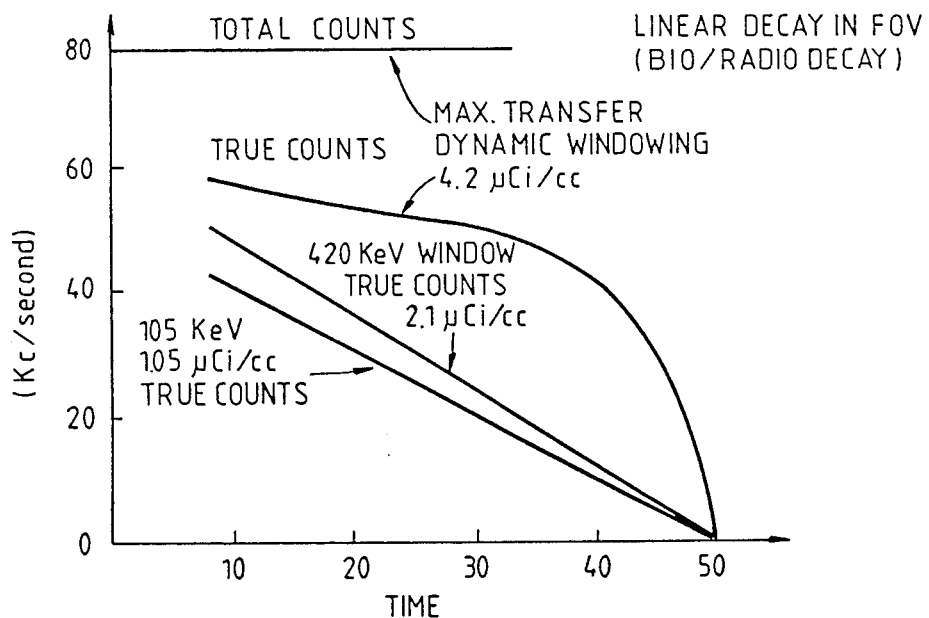
Fig. 7 LINEAR DECAY IN FOV (BIO/RADIO DECAY)
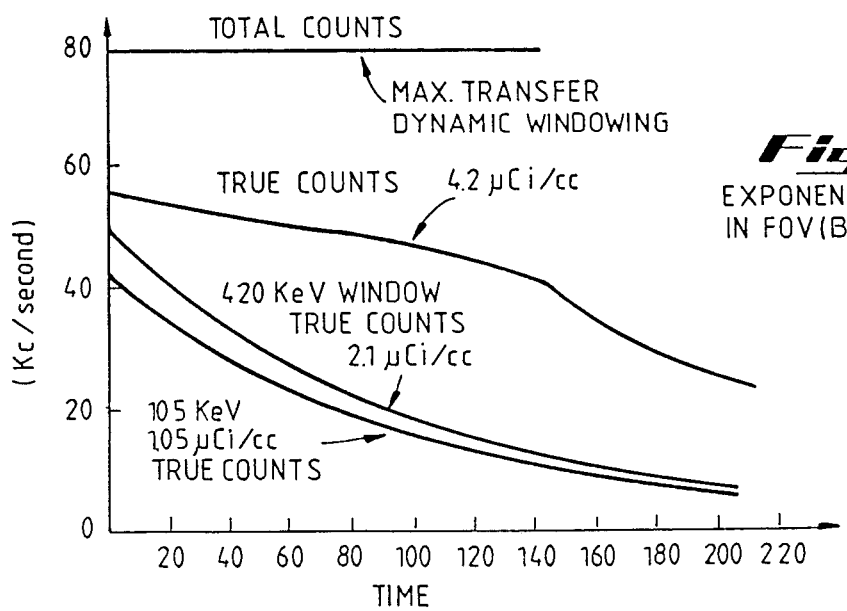
Fig. 8 EXPONENTIAL DECAY IN FOV (BIO/RADIO DECAY)

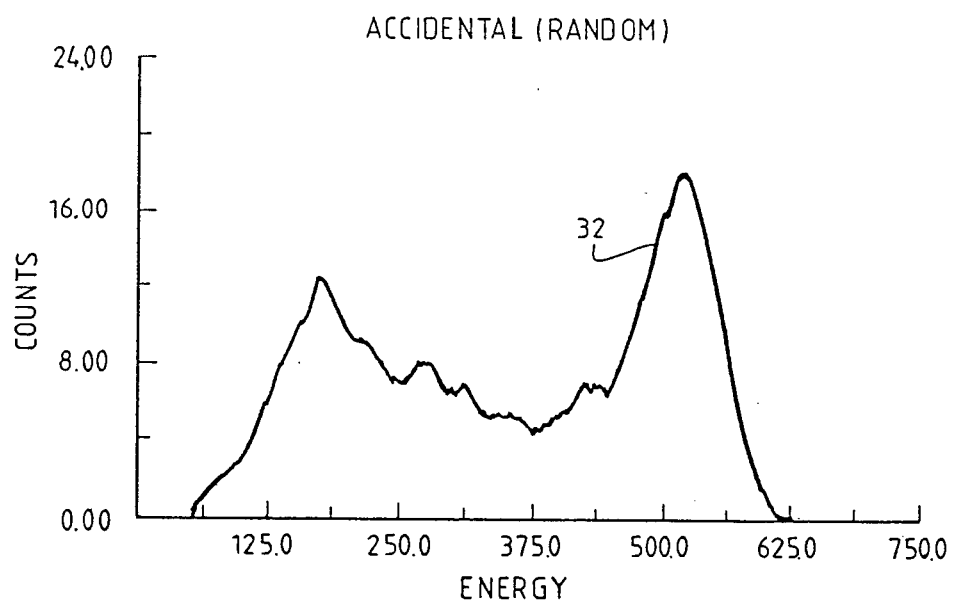
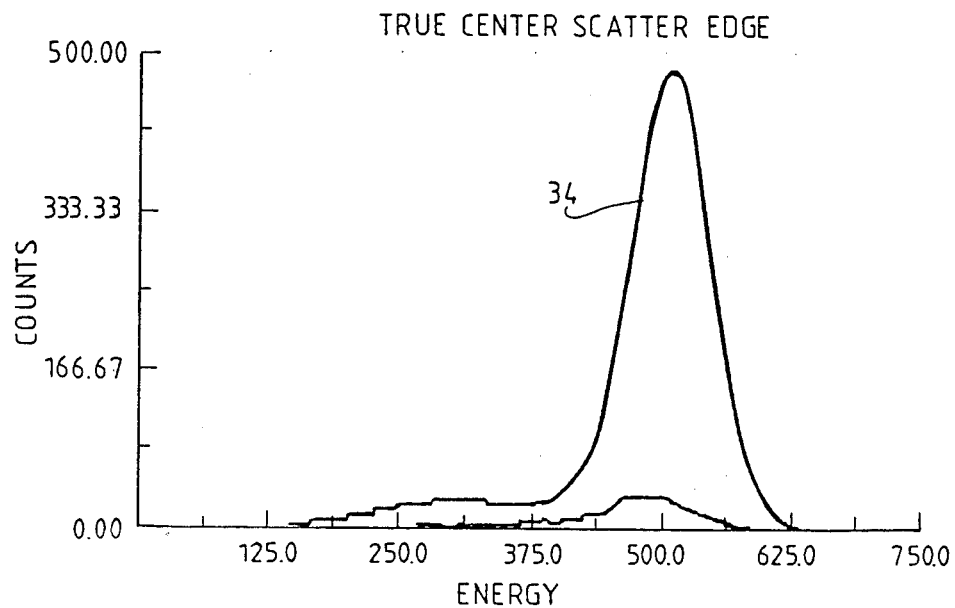

METHOD AND APPARATUS FOR MAXIMIZING COUNTS OF A PET CAMERA

BACKGROUND OF THE INVENTION

It is well known to utilize a positron emission tomography (PET) camera for measuring the concentrations of positron emitting radioisotopes inserted into a patient. Electromagnetic radiation is emitted in the form of two gamma rays of equal energy (511 keV), which are emitted 180° to each other. A count of this annihilation radiation is detected externally and is used to measure both the quantity and the location of the positron emitter.

One problem of the PET camera is that it measures, in addition to the true counts, background noise which includes random or accidental and scattered coincidences. These random counts and scatter counts constitute a significant portion of the total counts measured by the PET camera.

Another problem is that the current PET cameras are very expensive with the camera itself costing more than one million dollars and a cyclotron to produce radioisotopes costs two million dollars. The only PET blood flow radionuclear tracer which does not need the cyclotron is rubidium-82 (Rb-82). Using Rb-82, the PET technology can be potentially afforded if the cost of the PET camera can be lowered. However, Rb-82 has a short 66 seconds half life and the total counts collected are rather low even though the initial counts are high enough to saturate most cameras. To produce a good Rb-82 image, the primary requirement for the camera is the ability to transfer or process data at extremely high data rates to accomodate the very high initial Rb-82 activity. The required data processing capability is very expensive. This is especially the case if the first pass injection bolus is to be measured. No existing camera can measure this bolus input function without injecting a much lower dosage, which in turn sacrifices the later phase tissue uptake image.

Since the maximum PET camera data transfer capability is limited, it is conventional to inject only the maximum radioisotope activity into the patient which can be processed by the maximum transfer rate of the camera without saturation and the data collection continues until the activity/data rate is insignificantly low, which in the case of Rb-82 is typically about 3 minutes which lowers the statistical quality of the latter phase image.

The present method and apparatus is directed to providing a new PET data collection method which can improve image quality by approximately doubling the true counts and allows the PET camera to handle a larger dynamic range, for example, 4 or 5 times, of activity without saturation and without increasing the data processing capability of the PET camera, which is extremely expensive. And presently the camera sensitivity is already near the theoretical limit. Therefore, the present method appears to be the only viable way of increasing the detected true counts.

SUMMARY

The present method and apparatus is directed to more fully utilizing the maximum data transfer capability of the PET camera throughout most of the data collection period. The present method includes injecting a radioisotope activity into the patient which is several times higher than normal. At this activity level, the accidental noise count rate is several times higher than the true count rate and totally saturates the data transfer capability of the PET camera. However, this accidental noise has a lower energy spectrum distribution than the true counts. In the present method and apparatus the energy acceptance window of the camera is dynamically driven to a much higher level and since the noise level is attenuated much more than the true counts, the total data transfer rate is reduced down to within the transfer capability of the camera. Also, while the radioisotope activity decays rapidly, the accidental noise counts decays much faster than the true counts. Therefore, the energy acceptance window can be dynamically lowered for accepting true counts at the maximum data transfer capability of the camera even though the radioisotope activity is decaying rapidly. Calculations have shown that this will provide a two-fold increase in the true counts and a better image. Quantitation is still provided and the camera can be used to measure the first pass bolus input function without sacrificing the latter phase tissue uptake image. Quantitative dynamic study is allowed though the energy window is constantly varying because the energy detection response of the detector to true 511 KeV gamma can be measured on the bench and be used to normalize to a fixed energy window reference.

An object of the present invention is the provision of the method of operating a positron emission tomography camera for measuring concentrations of positron emitting radioisotopes from a patient which measures radiation including true counts, random counts, and scatter counts through an energy acceptance window in which the camera has a maximum camera transfer capability by measuring counts including measuring the total counts of radiation and varying the energy acceptance window to accept the total counts available at the maximum camera transfer capability.

A further object of the present invention is injecting an amount of radiation into the patient sufficient to normally initially saturate the maximum camera transfer capability. Preferably, the amount of radiation is at least four times the normal amount of radiation. In one embodiment of the invention, the positron emitting radioisotope is Rb-82.

Yet a still further object of the present invention is wherein the energy acceptance window is varied by the measurement of total counts.

Other and further objects, features and advantages will be apparent from the following description of a presently preferred embodiment of the invention, given for the purpose of disclosure and taken in conjunction with the accompanying drawings.

BRIEF DESCRIPTION OF THE DRAWINGS

FIG. 1 is a perspective elevational view of one type of positron emission tomography camera, FIG. 2 is a graph illustrating the comparison of measured counts between a prior art camera and a camera using the present invention, FIG. 7 is a graph illustrating the total counts collected for the maximum transfer case of the present invention and three conventional cases when the activity is decaying linearally, FIG. 8 is a graph similar to FIG. 7 but with the activity decaying exponentially, FIG. 9 illustrates the relationship between counts and energy for the accidental or random counts, and FIG. 10 is a graph illustrating the relationship between counts and energy for true counts and scatter counts.

DESCRIPTION OF THE PREFERRED EMBODIMENT

Figure 3:
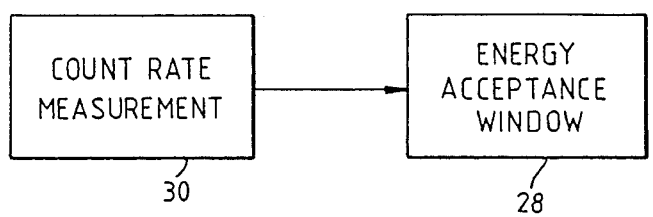
FIG. 3 is a schematic block diagram illustrating the control of the present invention.

Referring now to the drawings, and particularly to FIG. 1, the reference numeral 10 generally indicates a conventional positron emission tomography (PET) camera having a support gantry 12, a plurality of planes of detectors, here shown as rings 20, positioned side by side and surrounding a patient area 16 to detect radiation therefrom. The patient area 16 may include a patient bed 18 for supporting a patient within the rings of detector. In a PET camera, a positron isotope, such as Rb-82, is injected into the patient, each positron isotope atom then emits two gammas simultaneously and back-to-back. The detectors 20 then capture these gammas to produce an image of the tracer distribution.

The total counts for a PET camera include true, scatter, and random coincident counts. The charts and graphs illustrated in the specification are theoretical calculations for the counts made for a whole body camera with BGO crystals, 2 cm slice thickness, and a detector ring diameter of 90 cm. For most multi-ring PET camera, for example 5 rings, a typical maximum total count rate of 1,000,000 counts per second implies about 80-100 kc/second per image. That is, the camera has a maximum data transfer rate 22, as best seen in FIG. 2, which it can process without saturation. It is conventional to inject a maximum amount of a radioisotope that provides a count-time graph 24 which provides a maximum count activity less than the maximum data transfer rate 22 of the camera and the data collection continues timewise until the activity data rate is insignificantly low. Therefore, the number of counts is represented by the double cross hatch area under the graph 24. It is to be noted that the maximum data transfer capability 22 of the camera is not fully utilized throughout most of the data collection period and in particular in the latter stages of the data collection period. A larger range of radioisotope activity cannot be used without saturating a conventional camera or without increasing the camera sensitivity or increasing the data processing capability of the PET, all of which is extremely expensive. And in the case of the use of Rb-82 with its very high initial activity, no existing camera can measure the first pass injection bolus without injecting a low dosage, which in turn sacrifices the later phase tissue uptake image.

The present invention provides a new PET data collection method which can improve image quality by doubling the true counts and allow the PET camera to handle a 4–5 times larger dynamic range of radioisotope activity without saturation. The present method maintains the maximum data rate 22 even when the activity is decaying rapidly and thus the total counts collected will be greatly increased. The total counts collected are illustrated in FIG. 2 by the total cross-hatched area. A 2-times increase in true count is calculated for a 20 cm phantom. The present method requires injecting a radioisotope activity such as illustrated by the graph 26 which may be 4 times more than the normal. At this radioisotope activity level, the random noise count rate is several times higher than the true count rate and totally saturates the data transfer capability 22 of the camera. However this accidental or random noise has a lower energy spectrum distribution than the true counts. The present apparatus and method is directed to dynamically driving the energy acceptance window of the PET camera to a much higher level whereby the random noise level is attenuated much more than the true counts to bring the total data transfer rate down to the level 22 within the capability of the camera. Then, as the radioisotope activity, such as RB-82, decays rapidly, the accidental or random noise decays much faster than the true count rate as will be shown hereinafter. That is, while the true count rate decays as a function of time, the random counts decay as a square function of time. Hence, the energy window of the PET camera can be dynamically lowered to keep on accepting true counts at the same maximum allowable rate 22 even though the radio isotopeactivity is decaying rapidly. The camera can then be used to measure the first pass bolus input function without sacrificing the latter phase tissue uptake image.

Referring to FIG. 3, the PET energy acceptance window 28 is initially dynamically driven higher in response to the count rate measurement 30 to reject a portion of the scatter counts, the random counts, and some true counts. The window 28 should be driven high enough to lower the data rate down to the PET maximum data transfer limit 22 (FIG. 2). As the radioisotope activity decays, the accidentals decay faster than the true counts and the energy window is dynamically lowered to keep the data rate up to the maximum 22 (FIG. 2) throughout the measuring period.

Figure 4:
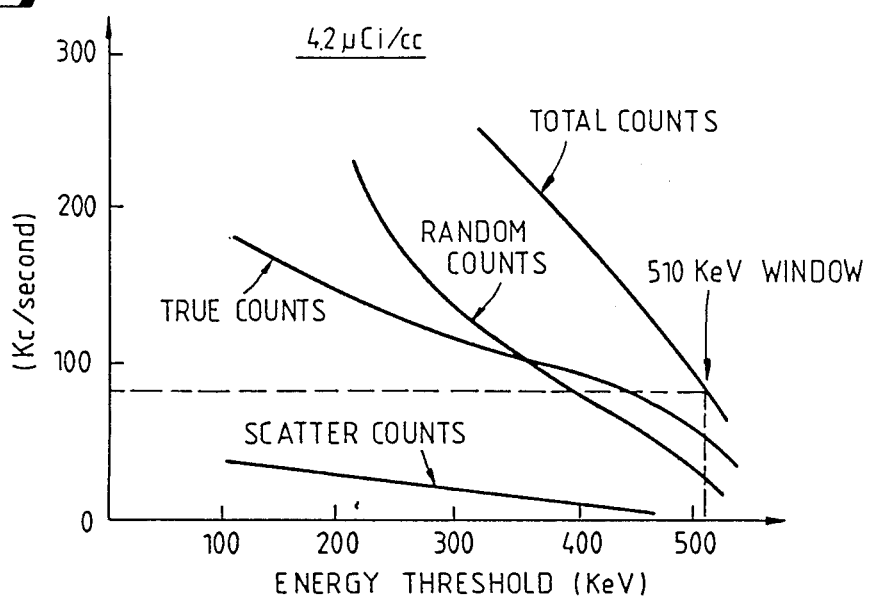
FIG. 4 is a graph illustrating the setting for the energy acceptance window for a radio activity of 4.2 $\mu$Ci/cm$^3$.

Referring now to FIG. 4, with the field of view activity density at 4.1 $\mu Ci/cm^3$ and with a maximum transfer rate of 80 kc/second per image, it is noted that the random count rate is initially higher than the true count rate and the total counts saturates the transfer capability of the camera. It is also noted that the random count decays at a much faster rate than the true counts rate. In this case, the energy window should be set to 510 KeV which, while maintaining the data count rate at the maximum camera data transfer capability, attenuates the random count much more than the true count and brings the total data transfer rate down to within the capability of the camera. This is shown in FIGS. 9 and 10 wherein a 510 KeV window will attentuate the accidental or random counts 32 to a greater extent than the true counts 34 in FIG. 10.

Figure 5:
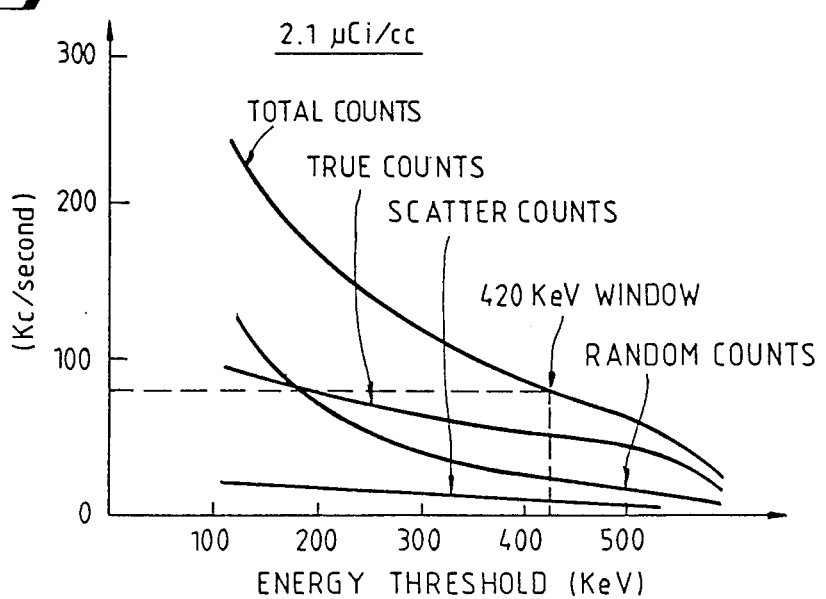
FIG. 5 is a graph illustrating the setting of the energy acceptance window for radio activity of 2.5 $\mu$Ci/cm$_3$.

Referring now to FIG. 5, with the radioisotope activity decayed to 2.1 $\mu Ci/cm^3$, the energy window should be set to a 420 KeV window. The graphs in FIG. 5 show that as the isotope activity decays rapidly, the accidental or random noise decays much faster than the true count rate. Hence, the energy window can be dynamically lowered to keep in accepting true counts at the same maximum allowable data transfer capability even though the isotope activity is decaying rapidly.

Figure 6:
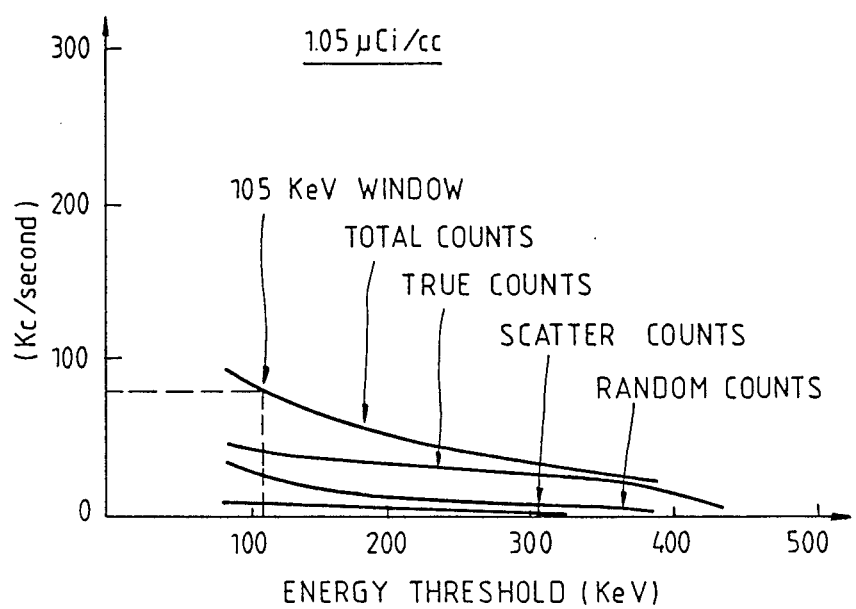
FIG. 6 is a graph illustrating the setting of the energy acceptance window for radio activity density of 1.05 $\mu Ci/cm^3$.

Referring now to FIG. 6, with the isotope density decayed to 1.05 $\mu Ci/cm^3$, the window should be set to 105 KeV. Because of the proximity of the 105 KeV window to lead X-ray, the window should not be lowered further.

Thus, with the energy window dynamically determined and set by the count rate measurement, the full data transfer capability of the camera is utilized throughout the data collection period. The noise/true ratio throughout the collection period with the dynamic windowing is about 1:2.

Referring now to FIG. 7, the total counts collected with the field of view (FOV) activity decaying linearally with time is shown for the maximum transfer case and three conventional cases as a function of data collection time. If data is collected through the relative time of 50, the maximum transfer case will have two times more counts than the conventional case (by comparing the area under the curves). With the isotope activity decaying exponentially, the acceptance rate is shown in FIG. 8 with the data collection period lasting 2 half lives, the true total counts collected for the maximum transfer method of the present invention is also about 2 times over the conventional methods. Since the energy detection response of a given crystal is fixed and measurable, the counts received at various energy windows can be normalized to that of a fixed window to allow dynamic quantitation over time.

Another benefit of the method of the present invention of data collection is the ability to handle a much larger dynamic range of activity in the field of view without losing quantitation. Hence even with a large bolus injection, one can quantitatively measure both the peak count and the later phase count. This kind of measurement would be impossible in conventional collection without lowering the initial dosage, which in turn sacrifices the statistical quality of the later phase image. Therefore, the present data collection method can improve the image quality in PET camera without actually improving the sensitivity or maximum data transfer capability of the camera, both of which can be extremely expensive.

The present invention, therefore, is well adapted to carry out the objects and attain the ends and advantages mentioned as well as others inherent therein. While a presently preferred embodiment of the invention has been given for the purpose of disclosure, numerous changes in the details of construction and arrangement of parts and steps of the method will be readily apparent to those skilled in the art and which are emcompassed within the spirit of the invention and the scope of the appended claims.

What is claimed is:

1. The method of operating a positron emission tomography camera for measuring concentrations of positron emitting radioisotopes which measure radiation from a patient including true counts, scatter counts and random counts through an energy acceptance window in which the camera has a maximum camera transfer capability of measuring counts comprising, measuring the total counts of radiation, and varying the energy acceptance window to accept the total counts available at the maximum camera transfer capability.

2. The method of claim 1 including, injecting an amount of radiation into the patient normally sufficient to initially saturate the maximum camera transfer capability.

3. The method of claim 2 wherein the amount of injection radiation is a least four times the normal amount of injection radiation.

4. The method of claim 3 wherein the positron emitting radioisotope is Rb-82.

5. The method of claim 2 wherein the energy acceptance window is varied by the measurement of total counts.

6. In a positron emission tomography camera, the improvement comprising, means for measuring the total counts of radiation injected into a patient including true counts, random counts and scatter counter, and an energy acceptance window, said window controlled by the measuring means for varying the window for accepting the total counts measured at the maximum camera transfer capability.

* * * * *